US011090019B2

(12) United States Patent
Siemionow et al.

(10) Patent No.: US 11,090,019 B2
(45) Date of Patent: Aug. 17, 2021

(54) AUTOMATED SEGMENTATION OF THREE DIMENSIONAL BONY STRUCTURE IMAGES

(71) Applicant: HOLO SURGICAL INC., Chicago, IL (US)

(72) Inventors: Krzysztof B. Siemionow, Chicago, IL (US); Cristian J. Luciano, Evergreen Park, IL (US); Marek Kraft, Poznan (PL)

(73) Assignee: Holo Surgical Inc., Chicago, IL (US)

( * ) Notice: Subject to any disclaimer, the term of this patent is extended or adjusted under 35 U.S.C. 154(b) by 545 days.

(21) Appl. No.: 16/154,747

(22) Filed: Oct. 9, 2018

(65) Prior Publication Data

US 2019/0105009 A1    Apr. 11, 2019

(30) Foreign Application Priority Data

Oct. 10, 2017  (EP) .................................... 17195826

(51) Int. Cl.
*G06K 9/00* (2006.01)
*A61B 6/00* (2006.01)
(Continued)

(52) U.S. Cl.
CPC ............ *A61B 6/5229* (2013.01); *A61B 6/032* (2013.01); *A61B 6/542* (2013.01); *G06T 3/4046* (2013.01);
(Continued)

(58) Field of Classification Search
CPC ....... A61B 6/5229; A61B 6/032; A61B 6/542; A61B 6/5258; G06T 7/11; G06T 3/4046;
(Continued)

(56) References Cited

U.S. PATENT DOCUMENTS 6,405,072 B1   6/2002  Cosman
8,314,815 B2  11/2012  Navab et al.
(Continued)

FOREIGN PATENT DOCUMENTS

CN     106600568      4/2017
EP     2 922 025 A1   9/2015
(Continued)

OTHER PUBLICATIONS

Cosmin Cernazanu-Glavan et al. "Segmentation of Bone Structure in X-ray Images Using Conventional Neural Network" Advances in Electrical and Computer Engineering vol. 13, No. 1, 2013. DOI:10.4316/AECE.2013.01015.
(Continued)

*Primary Examiner* — Charlotte M Baker

(57) ABSTRACT

A computer-implemented system: at least one processor communicably coupled to at least one nontransitory processor-readable storage medium storing processor-executable instructions or data receives segmentation learning data comprising a plurality of batches of labeled anatomical image sets, each image set comprising image data representative of a series of slices of a three-dimensional bony structure, and each image set including at least one label which identifies the region of a particular part of the bony structure depicted in each image of the image set, wherein the label indicates one of a plurality of classes indicating parts of the bone anatomy; trains a segmentation CNN, that is a fully convolutional neural network model with layer skip connections, to segment semantically at least one part of the bony structure utilizing the received segmentation learning data; and stores the trained segmentation CNN in at least one nontransitory processor-readable storage medium of the machine learning system.

20 Claims, 8 Drawing Sheets

(51) Int. Cl.
*G06T 3/40* (2006.01)
*A61B 6/03* (2006.01)
*G06T 7/11* (2017.01)
G06T 5/50 (2006.01)
G06T 11/00 (2006.01)
G06K 9/66 (2006.01)
G06T 5/00 (2006.01)

(52) U.S. Cl.
CPC ............... *G06T 7/11* (2017.01); *A61B 6/5258* (2013.01); *G06K 9/66* (2013.01); *G06T 5/002* (2013.01); *G06T 5/50* (2013.01); *G06T 11/008* (2013.01); *G06T 2207/10081* (2013.01); *G06T 2207/20084* (2013.01); *G06T 2207/30012* (2013.01)

(58) Field of Classification Search
CPC . G06T 2207/20084; G06T 2207/30012; G06T 2207/10081; G06T 5/50; G06T 11/008; G06T 5/002; G06K 9/66
USPC ...................... 382/131; 378/20; 600/439, 443
See application file for complete search history.

(56) References Cited

U.S. PATENT DOCUMENTS

| | | |
|---|---|---|
| 8,933,935 B2 | 1/2015 | Yang et al. |
| 9,289,267 B2 | 3/2016 | Sauer et al. |
| 9,532,848 B2 | 1/2017 | Amiot et al. |
| 9,949,700 B2 | 4/2018 | Razzaque et al. |
| 10,016,243 B2 | 7/2018 | Esterberg |
| 10,080,623 B2 | 9/2018 | Saito et al. |
| 10,105,187 B2 | 10/2018 | Corndorf et al. |
| 10,646,283 B2 | 5/2020 | Johnson et al. |
| 10,646,285 B2 | 5/2020 | Siemionow et al. |
| 10,653,497 B2 | 5/2020 | Crawford et al. |
| 10,788,672 B2 | 9/2020 | Yadav et al. |
| 10,939,977 B2 | 3/2021 | Messinger et al. |
| 10,951,872 B2 | 3/2021 | Casas |
| 2002/0082498 A1 | 6/2002 | Wendt et al. |
| 2004/0047044 A1 | 3/2004 | Dalton |
| 2005/0190446 A1 | 9/2005 | Kuerz et al. |
| 2005/0289472 A1 | 12/2005 | Morita et al. |
| 2006/0176242 A1 | 8/2006 | Jaramaz et al. |
| 2008/0144773 A1 | 6/2008 | Bar-Zohar et al. |
| 2010/0328433 A1 | 12/2010 | Li |
| 2011/0229005 A1 | 9/2011 | Harder et al. |
| 2012/0314224 A1 | 12/2012 | Luellau |
| 2013/0226190 A1 | 8/2013 | Mckinnon et al. |
| 2015/0018622 A1 | 1/2015 | Tesar et al. |
| 2015/0177598 A1 | 6/2015 | Mime et al. |
| 2015/0264339 A1 | 9/2015 | Riedel |
| 2016/0035139 A1 | 2/2016 | Fuchs et al. |
| 2016/0176242 A1 | 6/2016 | Nakamata |
| 2016/0187969 A1 | 6/2016 | Larsen et al. |
| 2016/0191887 A1 | 6/2016 | Casas |
| 2016/0278875 A1 | 9/2016 | Crawford et al. |
| 2016/0324580 A1 | 11/2016 | Esterberg |
| 2016/0328630 A1 | 11/2016 | Han et al. |
| 2017/0024903 A1 | 1/2017 | Razzaque |
| 2017/0042631 A1 | 2/2017 | Doo et al. |
| 2017/0056115 A1 | 3/2017 | Corndorf et al. |
| 2017/0084036 A1 | 3/2017 | Pheiffer et al. |
| 2017/0112575 A1 | 4/2017 | Li et al. |
| 2017/0258526 A1 | 9/2017 | Lang |
| 2017/0323062 A1 | 11/2017 | Djajadiningrat et al. |
| 2017/0329402 A1 | 11/2017 | Riedel |
| 2017/0360395 A1 | 12/2017 | Razzaque |
| 2018/0012416 A1 | 1/2018 | Jones et al. |
| 2018/0078316 A1 | 3/2018 | Schaewe et al. |
| 2018/0082480 A1 | 3/2018 | White et al. |
| 2018/0140362 A1 | 5/2018 | Cali et al. |
| 2018/0174311 A1 | 6/2018 | Kluckner et al. |
| 2018/0225993 A1 | 8/2018 | Buras et al. |
| 2018/0271484 A1 | 9/2018 | Whisler |
| 2018/0303558 A1 | 10/2018 | Thomas |
| 2018/0311012 A1 | 11/2018 | Moctezuma et al. |
| 2019/0029757 A1 | 1/2019 | Roh et al. |
| 2019/0053851 A1 | 2/2019 | Siemionow et al. |
| 2019/0130575 A1 | 5/2019 | Chen et al. |
| 2019/0142519 A1 | 5/2019 | Siemionow et al. |
| 2019/0175285 A1 | 6/2019 | Siemionow et al. |
| 2019/0192230 A1 | 6/2019 | Siemionow et al. |
| 2019/0201106 A1 | 7/2019 | Siemionow et al. |
| 2019/0307513 A1 | 10/2019 | Leung et al. |
| 2019/0333626 A1* | 10/2019 | Mansi ................ A61B 5/746 |
| 2020/0051274 A1 | 2/2020 | Siemionow et al. |
| 2020/0151507 A1 | 5/2020 | Siemionow et al. |
| 2020/0229877 A1 | 7/2020 | Siemionow et al. |
| 2020/0327721 A1 | 10/2020 | Siemionow et al. |
| 2020/0410687 A1 | 12/2020 | Siemionow et al. |

FOREIGN PATENT DOCUMENTS

| | | |
|---|---|---|
| EP | 3 151 736 A2 | 4/2017 |
| EP | 3 221 809 A1 | 9/2017 |
| EP | 3 361 979 A1 | 8/2018 |
| EP | 3 432 263 A1 | 1/2019 |
| GB | 2 536 650 A | 9/2016 |
| WO | WO 2007/110820 A2 | 10/2007 |
| WO | WO 2007/115826 A2 | 10/2007 |
| WO | WO 2012/018560 A2 | 2/2012 |
| WO | WO 2012/027574 A1 | 3/2012 |
| WO | 2014036473 | 3/2014 |
| WO | WO 2015/058816 A1 | 4/2015 |
| WO | WO 2016/010737 A2 | 1/2016 |
| WO | WO 2016/078919 A1 | 5/2016 |
| WO | WO 2017/003453 A1 | 1/2017 |
| WO | WO 2017/066373 A1 | 4/2017 |
| WO | WO 2017/091833 A1 | 6/2017 |
| WO | WO 2018/048575 A1 | 3/2018 |
| WO | WO 2018/052966 A1 | 3/2018 |
| WO | WO 2018/057564 A1 | 3/2018 |
| WO | WO 2018/063528 A1 | 4/2018 |
| WO | WO 2018/140415 A1 | 8/2018 |
| WO | WO 2019/005722 A1 | 1/2019 |
| WO | WO 2019/195926 A1 | 10/2019 |

OTHER PUBLICATIONS

Hu Chen et al. "Low-dose CT denoising with convolutional neural network" 2017 IEEE 14th International Symposium on Biomedical Imaging (ISBI 2017). DOI: 10.1109/ISBI.2017.7950488.
U.S. Appl. No. 16/101,459, filed Aug. 12, 2018.
U.S. Appl. No. 16/217,073, filed Dec. 12, 2018.
U.S. Appl. No. 16/186,549, filed Nov. 11, 2018.
U.S. Appl. No. 17/145,178, filed Jan. 8, 2021.
U.S. Appl. No. 16/217,061, filed Dec. 12, 2018.
U.S. Appl. No. 16/236,663, filed Dec. 31, 2018.
U.S. Appl. No. 16/537,645, filed Aug. 12, 2019.
U.S. Appl. No. 16/677,707, filed Nov. 8, 2019.
U.S. Appl. No. 16/833,750, filed Mar. 30, 2020.
U.S. Appl. No. 16/897,315, filed Jun. 10, 2020.
Non-Final Office Action dated Nov. 16, 2020 for U.S. Appl. No. 16/101,459, 43 pages.
Non-Final Office Action dated Sep. 16, 2019 for U.S. Appl. No. 16/059,061, 20 pages.
Non-Final Office Action dated Jul. 10, 2020 for U.S. Appl. No. 16/842,793, 23 pages.
Non-Final Office Action dated Oct. 28, 2020 for U.S. Appl. No. 16/186,549, 30 pages.
Non-Final Office Action dated Oct. 27, 2020 for U.S. Appl. No. 16/537,645, 18 pages.
Extended European Search Report dated Oct. 25, 2017 for European Application No. 17186306.1, 14 pages.
Extended European Search Report dated Oct. 27, 2017 for European Application No. 17186307.9, 15 pages.
Extended European Search Report dated Feb. 16, 2018 for European Application No. 17195826.7, 8 pages.

(56) References Cited

OTHER PUBLICATIONS

Extended European Search Report dated Feb. 12, 2018 for European Application No. 17201224.7, 14 pages.
Extended European Search Report dated Feb. 27, 2018 for European Application No. 17206558.3, 13 pages.
Communication Pursuant to Article 94(3) dated Mar. 18, 2020 for European Application No. 17206558.3, 11 pages.
Extended European Search Report dated Apr. 17, 2019 for European Application No. 18211806.7, 8 pages.
Communication Pursuant to Article 94(3) dated Apr. 22, 2020 for European Application No. 18211806.7, 6 pages.
Extended European Search Report dated Jul. 5, 2018 for European Application No. 18150376.4, 10 pages.
Extended European Search Report dated Feb. 26, 2019 for European Application No. 18188557.5, 9 pages.
Extended European Search Report dated Feb. 1, 2019 for European Application No. 18205207.6, 9 pages.
Extended European Search Report dated Nov. 4, 2019 for European Application No. 19169136.9, 5 pages.
Extended European Search Report dated Oct. 23, 2019 for European Application No. 19179411.4, 8 pages.
Christ, P. F. et al., "Automatic Liver and Lesion Segmentation in CT Using Cascaded Fully Convolutional Neural Networks and 3D Conditional Random Fields," Oct. 7, 2016, 8 pages; arXiv:1610.02177v1.
Cramer, J., "Medical Image Segmentation and Design Tutorial with MevisLab," Apr. 27, 2016, retrieved on Jan. 26, 2018 from https://www.youtube.com/watch?v=PHf3Np37zTW, 1 page.
Egmont-Petersen, M. & Arts, T., "Recognition of radiopaque markers in X-ray images using a neural network as nonlinear filter," Pattern Recognition Letters, 20:521-533 (1999).
Fitzpatrick, J. M., "The role of registration in accurate surgical guidance," Proceedings of the Institute of Mechanical Engineering Medicine, Part H: Journal of Engineering in Medicine, 224(5):607-622 (2010); doi:10.1243/09544119JEIM589.
Gros, C. et al., "Automatic segmentation of the spinal cord and intramedullary multiple sclerosis lesions with convolutional neural networks," Neuroimage, 184:901-915 (2019).
Han, Z. et al, "Spine-GAN: Semantic segmentation of multiple spinal structures," Med Image Anal., 50:23-35 (2018); doi:10.1016/j.media.2018.08.005. Epub Aug. 25, 2018.
Jiménez-Pastor, A. et al., "Automatic localization and identification of vertebrae in spine CT scans by combining Deep Learning with morphological image processing techniques," European Congress of Radiology (ECR) 2018, Mar. 4, 2018, retrieved from the Internet at: https://quibim.com/wp-content/uploads/2018/03/3_ECR2018_AJP, 30 pages.
Krinninger, M., "Ein System zur Endoskopführung in der HNO-Chirurgie," Dissertation, Mar. 15, 2011, XP055450605, Technischen Universität München, 151 pages.
Krinninger, M., "Ein System zur Endoskopführung in der HNO-Chirurgie," Dissertation, Mar. 15, 2011, XP055450605, Technischen Universität München; retrieved on Feb. 13, 2018 from https://mediatum.ub.tum.de/doc/998215/998215.pdf.—English Abstract, 1 page.
Krishnan, R. et al., "Automated Fiducial Marker Detection for Patient Registration in Image-Guided Neurosurgery," Computer Aided Surgery, 8(1):17-23 (2003).
Liu, Yanfeng et al., "Human-Readable Fiducial Marker Classification using Convolutional Neural Networks," 2017 IEEE International Conference on Electro Information Technology (EIT), IEEE, May 14, 2017, 5 pages.
Lootus, M. et al., "Vertebrae Detection and Labelling in Lumbar MR Images," Jan. 1, 2014, 12 pages.
Mao, X. -J. et al, "Image Restoration Using Very Deep Convolutional Encoder-Decoder Networks with Symmetric Skip Connections," 29th Conference on Neural Information Processing Systems (NIPS 2016), Barcelona, Spain, 9 pages.
Shi, R. et al., "An Efficient Method for Segmentation of MRI Spine Images," IEEE/ICME International Conference on Complex Medical Engineering, Jun. 2007, 6 pages; doi:10.1109/ICCME.2007.4381830.
Song, Yuheng & Hao, Yan, "Image Segmentation Algorithms Overview," Jul. 7, 2017, retrieved from the Internet at: https://arxiv.org/ftp/arxiv/papers/1707/1707.02051, 6 pages.
Yang, D. et al., "Deep Image-to-Image Recurrent Network with Shape Basis Learning for Automatic Vertebra Labeling in Large-Scale 3D CT Volumes," Conference: International Conference on Medical Image Computing and Computer-Assisted Intervention, doi:10.1007/978-3-319-66179-7_57, Sep. 2017, 9 pages.
Communication under Rule 71(3) Intent to Grant dated Jan. 3, 2020 for European Application No. 17195826.7, 56 pages.
Non-Final Office Action dated Apr. 28, 2021 for U.S. Appl. No. 16/217,073, 12 pages.
Non-Final Office Action dated Mar. 25, 2021 for U.S. Appl. No. 16/217,061, 25 pages.

* cited by examiner

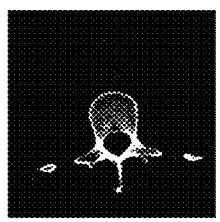 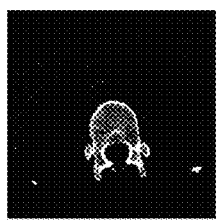 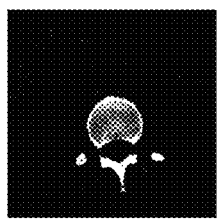 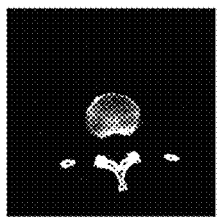 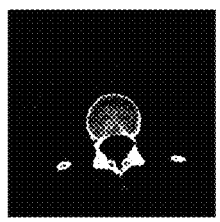
Fig. 1A  Fig. 1B  Fig. 1C  Fig. 1D  Fig. 1E
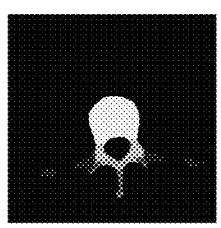 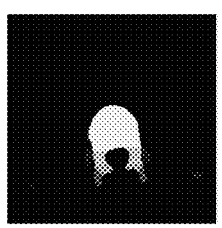 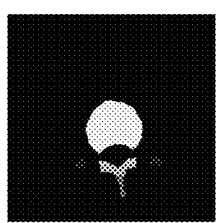 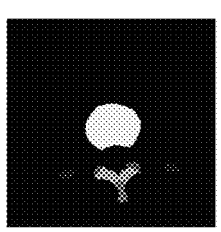 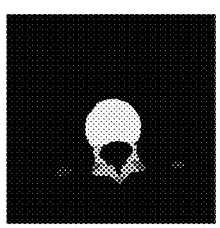
Fig. 1F  Fig. 1G  Fig. 1H  Fig. 1I  Fig. 1J
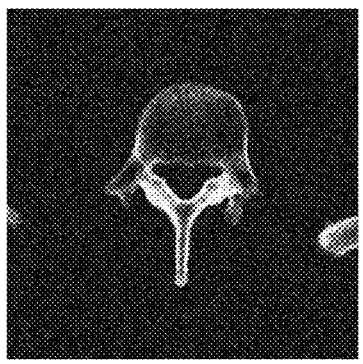 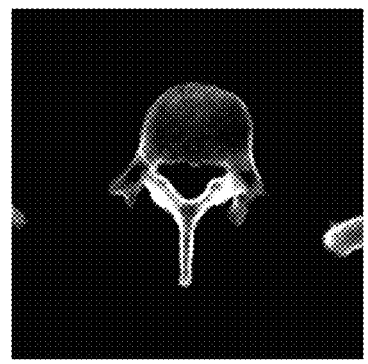
Fig. 2A  Fig. 2B
 
Fig. 2C  Fig. 2D

AUTOMATED SEGMENTATION OF THREE DIMENSIONAL BONY STRUCTURE IMAGES

TECHNICAL FIELD

The present disclosure generally relates to automated segmentation of three dimensional images of a bony structure, useful in particular for the field of computer assisted surgery, diagnostics, and surgical planning.

BACKGROUND

Image guided or computer assisted surgery is a surgical procedure where the surgeon uses tracked surgical instruments in conjunction with preoperative or intraoperative images in order to indirectly guide the procedure. Image guided surgery can utilize images acquired intraoperatively, provided for example from computer tomography (CT) scanners.

Specialized computer systems can be used to process the CT images to develop three-dimensional models of the anatomy fragment subject to the surgery procedure.

For this purpose, various machine learning technologies are developed, such as a convolutional neural network (CNN) that is a class of deep, feed-forward artificial neural networks. CNNs use a variation of multilayer perceptrons designed to require minimal preprocessing.

In the field of image guided surgery, low quality images may make it difficult to adequately identify key anatomic landmarks, which may in turn lead to decreased accuracy and efficacy of the navigated tools and implants. Furthermore, low quality image datasets may be difficult to use in machine learning applications.

Computer Tomography (CT) is a common method for generating a three dimensional (3D) image of a spine. CT scanning works like other x-ray examinations. Very small, controlled amounts of x-ray radiation are passed through the body, and different tissues absorb radiation at different rates. With plain radiology, when special film is exposed to the absorbed x-rays, an image of the inside of the body is captured. With CT, the film is replaced by an array of detectors, which measure the x-ray profile.

Inside the CT scanner is a rotating gantry that has an x-ray tube mounted on one side and an arc-shaped detector mounted on the opposite side. An x-ray beam is emitted in a fan shape as the rotating frame spins the x-ray tube and detector around the patient. Each time the x-ray tube and detector make a 360° rotation and the x-ray passes through the patient's body, the image of a thin section is acquired. During each rotation, the detector records about 1,000 images (profiles) of the expanded x-ray beam. Each profile is then reconstructed by a dedicated computer into a 3-dimensional image of the section that was scanned. The speed of gantry rotation, along with slice thickness, contributes to the accuracy/usefulness of the final image.

Commonly used intraoperative scanners have a variety of settings that allow for control of radiation dose. In certain scenarios high dose settings may be chosen to ensure adequate visualization of all the anatomical structures. The downside is increased radiation exposure to the patient. The effective doses from diagnostic CT procedures are typically estimated to be in the range of 1 to 10 mSv (millisieverts). This range is not much less than the lowest doses of 5 to 20 mSv estimated to have been received by survivors of the atomic bombs. These survivors, who are estimated to have experienced doses slightly larger than those encountered in CT, have demonstrated a small but increased radiation-related excess relative risk for cancer mortality.

The risk of developing cancer as a result of exposure to radiation depends on the part of the body exposed, the individual's age at exposure, and the individual's gender. For the purpose of radiation protection, a conservative approach that is generally used is to assume that the risk for adverse health effects from cancer is proportional to the amount of radiation dose absorbed and that there is no amount of radiation that is completely without risk.

Low dose settings should be therefore selected for computer tomography scans whenever possible to minimize radiation exposure and associated risk of cancer development. However, low dose settings may have an impact on the quality of the final image available for the surgeon. This in turn can limit the value of the scan in diagnosis and treatment.

Magnetic resonance imaging (MRI) scanner forms a strong magnetic field around the area to be imaged. In most medical applications, protons (hydrogen atoms) in tissues containing water molecules create a signal that is processed to form an image of the body. First, energy from an oscillating magnetic field temporarily is applied to the patient at the appropriate resonance frequency. The excited hydrogen atoms emit a radio frequency signal, which is measured by a receiving coil. The radio signal may be made to encode position information by varying the main magnetic field using gradient coils. As these coils are rapidly switched on and off they create the characteristic repetitive noise of an MRI scan. The contrast between different tissues is determined by the rate at which excited atoms return to the equilibrium state. Exogenous contrast agents may be given intravenously, orally, or intra-articularly.

The major components of an MRI scanner are: the main magnet, which polarizes the sample, the shim coils for correcting inhomogeneities in the main magnetic field, the gradient system which is used to localize the MR signal and the RF system, which excites the sample and detects the resulting NMR signal. The whole system is controlled by one or more computers.

The most common MRI strengths are 0.3 T, 1.5 T and 3 T. The "T" stands for Tesla—the unit of measurement for the strength of the magnetic field. The higher the number, the stronger the magnet. The stronger the magnet the higher the image quality. For example, a 0.3 T magnet strength will result in lower quality imaging then a 1.5 T. Low quality images may pose a diagnostic challenge as it may be difficult to identify key anatomical structures or a pathologic process. Low quality images also make it difficult to use the data during computer assisted surgery. Therefore it is important to have the ability to deliver a high quality MR image for the physician.

SUMMARY OF THE INVENTION

One aspect of the invention is a method of operating a machine learning system may include at least one nontransitory processor-readable storage medium that may store at least one of processor-executable instructions or data, and at least one processor communicably coupled to at least one nontransitory processor-readable storage medium. This method may be summarized as including:

receiving, by at least one processor, segmentation learning data comprising a plurality of batches of labeled anatomical image sets, each image set comprising image data representative of a series of slices of a three-dimensional bony structure, and each image set including at least one label which identifies the region of a particular part of the bony structure depicted in each image of the image set, wherein the label indicates one of a plurality of classes indicating parts of the bone anatomy;

training, by at least one processor, a segmentation CNN, that is a fully convolutional neural network model with layer skip connections, to segment semantically at least one part of the bony structure utilizing the received learning data; and storing, by at least one processor, the trained segmentation CNN in at least one nontransitory processor-readable storage medium of the machine learning system.

Another version of this aspect of the invention is a method of automated segmentation of images of a three-dimensional bony structure may include receiving, by at least one processor communicably coupled to at least one nontransitory processor-readable storage medium that stores at least one of processor-executable instructions or data, segmentation learning data comprising a plurality of batches of labeled anatomical image sets, each image set comprising image data representative of a series of slices of the three-dimensional bony structure, and each image set including at least one label which identifies the region of a particular part of the bony structure depicted in each image of the image set, wherein the label indicates one of a plurality of classes indicating parts of the bone anatomy. This method may also include training, by the at least one processor, a segmentation CNN, that is a fully convolutional neural network model with layer skip connections, to segment into a plurality of classes at least one part of the bony structure utilizing the received learning data. This method may further include storing, by the at least one processor, the trained segmentation CNN in the at least one nontransitory processor-readable storage medium.

Training the CNN model may include training a CNN model including a contracting path and an expanding path. The contracting path may include a number of convolutional layers, a number of pooling layers and dropout layers. Each pooling and dropout layer may be preceded by at least one convolutional layer. The expanding path may include a number of convolutional layers, a number of upsampling layers and a concatenation of feature maps from previous layers. Each upsampling layer may be preceded by at least one convolutional layer and may include a transpose convolution operation which performs upsampling and interpolation with a learned kernel.

Training a CNN model may include training a CNN model to segment at least one part of the anatomical structure utilizing the received learning data and, subsequent to each upsampling layer, the CNN model may include a concatenation of feature maps from a corresponding layer in the contracting path through a skip connection. Receiving learning data may include receiving preoperative or intraoperative images of the bony structure. Training a CNN model may include training a CNN model to segment at least one part of the anatomical structure utilizing the received learning data, and the CNN model may include a contracting path which may include a first convolutional layer, which may have between 1 and 256 feature maps. Training a CNN model may include training a CNN model which may include a plurality of convolutional layers to segment at least one part of the anatomical structure of the vertebrae utilizing the received learning data, and each convolutional layer may include a convolutional kernel of sizes $2n+1 \times 2n+1$, with n being a natural number, and a selectable stride. Training a CNN model may include training a CNN model which may include a plurality of pooling layers to segment at least one part of the anatomical structure utilizing the received learning data, and each pooling layer may include a $n \times n$ maximum or other type of pooling, with a selectable stride, with n being a natural number.

A CNN model may include training a CNN model to segment at least one part of the anatomical structure utilizing the received learning data, and the CNN model may include a plurality of pooling layers and a plurality of upsampling layers.

A CNN model may include training a CNN model which may include a plurality of convolutional layers to segment at least one part of the anatomical structure utilizing the received learning data, and the CNN model may pad the input to each convolutional layer using a zero padding operation.

A CNN model may include training a CNN model to segment at least one part of the anatomical structure utilizing the received learning data, and the CNN model may include a plurality of nonlinear activation function layers. The method may further include augmenting, by at least one processor, the learning data via modification of at least some of the image data in the plurality of batches of labeled image sets.

The method may further include modifying, by at least one processor, at least some of the image data in the plurality of batches of labeled image sets according to at least one of: a horizontal flip, a vertical flip, a shear amount, a shift amount, a zoom amount, a rotation amount, a brightness level, or a contrast level, additive noise of Gaussian and/or Poisson distribution and Gaussian blur.

The CNN model may include a plurality of hyperparameters stored in at least one nontransitory processor-readable storage medium, and may further include configuring, by at least one processor, the CNN model according to a plurality of configurations; for each of the plurality of configurations, validating, by at least one processor, the accuracy of the CNN model; and selecting, by at least one processor, at least one configuration based at least in part on the accuracies determined by the validations.

The methods may further include for each image set, identifying, by at least one processor, whether the image set is missing a label for any of a plurality of parts of the anatomical structure; and for image sets identified as missing at least one label, modifying, by at least one processor, a training loss function to account for the identified missing labels. Receiving learning data may include receiving image data which may include volumetric images, and each label may include a volumetric label mask or contour.

A CNN model may include training a CNN model which may include a plurality of convolutional layers to segment at least one part of the anatomical structure utilizing the received learning data, and each convolutional layer of the CNN model may include a convolutional kernel of size $N \times N \times K$ pixels, where N and K are positive integers.

A CNN model may include training a CNN model which may include a plurality of convolutional layers to segment at least one part of the anatomical structure utilizing the received learning data, and each convolutional layer of the CNN model may include a convolutional kernel of size $N \times M$ pixels, where N and M are positive integers. Receiving learning data may include receiving image data representative of labeled anatomical parts. Training a CNN model may include training a CNN model to segment at least one part of the anatomical structure utilizing the received learning data, and for each processed image, the CNN model may utilize data for at least one image which is at least one of: adjacent to the processed image with respect to space Another aspect of the invention is a method of operating a machine learning system that may include at least one nontransitory processor-readable storage medium that stores at least one of processor-executable instructions or data, and at least one processor communicably coupled to at least one nontransitory processor-readable storage medium. The method may be summarized as including receiving, by at least one processor, image data which represents an anatomical structure (for example a three-dimensional bony anatomical structure); processing, by at least one processor, the received image data through a fully convolutional neural network (CNN) model to generate per-class probabilities for each pixel of each image of the image data, each class corresponding to one of a plurality of parts of the anatomical structure represented by the image data; and for each image of the image data, generating, by at least one processor, a probability map for each of the plurality of classes using the generated per-class probabilities; and storing, by at least one processor, the generated probability maps in at least one nontransitory processor-readable storage medium.

Processing the received image data through the CNN model may include processing the received image data through a CNN model which may include a contracting path and an expanding path. The contracting path may include a number of convolutional layers and a number of pooling layers, each pooling layer preceded by at least one convolutional layer. The expanding path may include a number of convolutional layers and a number of upsampling layers, each upsampling layer preceded by at least one convolutional layer, and may include a transpose convolution operation which performs upsampling and interpolation with a learned kernel. Receiving image data may include, for example, receiving image data that is representative of a vertebrae in a spine. The methods may further include autonomously causing, by the at least one processor, an indication of at least one of the plurality of parts of the anatomical structure to be displayed on a display based at least in part on the generated probability maps.

The method may further include post-processing, by at least one processor, the processed image data to ensure at least one physical constraint is met. Receiving image data may include, for example, receiving image data that may be representative of vertebrae, and at least one physical constraint may include at least one of: constraints on the volumes of anatomical parts of the bony structure, such as a spine, coincidence and connections of the anatomical parts of the vertebrae, such as the vertebral body must be connected to two pedicles, spinous process must be connected to the lamina and cannot be connected to the vertebral body etc.

The method may further include for each image of the image data, transforming, by at least one processor, the plurality of probability maps into a label mask by setting the class of each pixel to the class with the highest probability.

The method may further include for each image of the image data, setting, by at least one processor, the class of each pixel to a background class when all of the class probabilities for the pixel are below a determined threshold.

The method may further include for each image of the image data, setting, by at least one processor, the class of each pixel to a background class when the pixel is not part of a largest connected region for the class to which the pixel is associated.

The method may further include converting, by at least one processor, each of the label masks for the image data combined into a 3D volume and further converting it into an alternative representation in the form of a polygonal mesh.

The method may further include autonomously causing, by at least one processor, the generated mesh to be displayed with the image data on a display.

The method may further include receiving, by at least one processor, a user modification of at least one of the displayed volumes and/or meshes in terms of change of color, opacity, changing the mesh decimation; and storing, by at least one processor, the modified volumes and/or meshes in at least one nontransitory processor-readable storage medium. The method may further include determining, by at least one processor, the volume of at least one of the plurality of parts of the anatomical structure utilizing the generated volume or mesh.

The method may further include causing, by at least one processor, the determined volume of at least one of the plurality of parts of the anatomical structure to be displayed on a display. Receiving image data may include receiving volumetric image data or polygonal mesh data. Processing the received image data through a CNN model may include processing the received image data through a CNN model in which each convolutional layer may include a convolutional kernel of sizes N×N×K pixels, where N and K are positive integers.

These and other features, aspects and advantages of the invention will become better understood with reference to the following drawings, descriptions and claims.

BRIEF DESCRIPTION OF DRAWINGS

Various embodiments are herein described, by way of example only, with reference to the accompanying drawings, wherein:

FIGS. 1A-1E show examples of various CT images of a spine and FIGS. 1F-1J show their corresponding segmented images in accordance with an embodiment of the invention;

FIGS. 2A and 2B show an enlarged view of a LDCT scan and HDCT scan in accordance with an embodiment of the invention;

FIG. 2C shows a low power magnetic resonance scan of a neck portion and FIG. 2D shows a higher power magnetic resonance scan of the same neck portion in accordance with an embodiment of the invention;

DETAILED DESCRIPTION OF THE INVENTION

Figure 3:
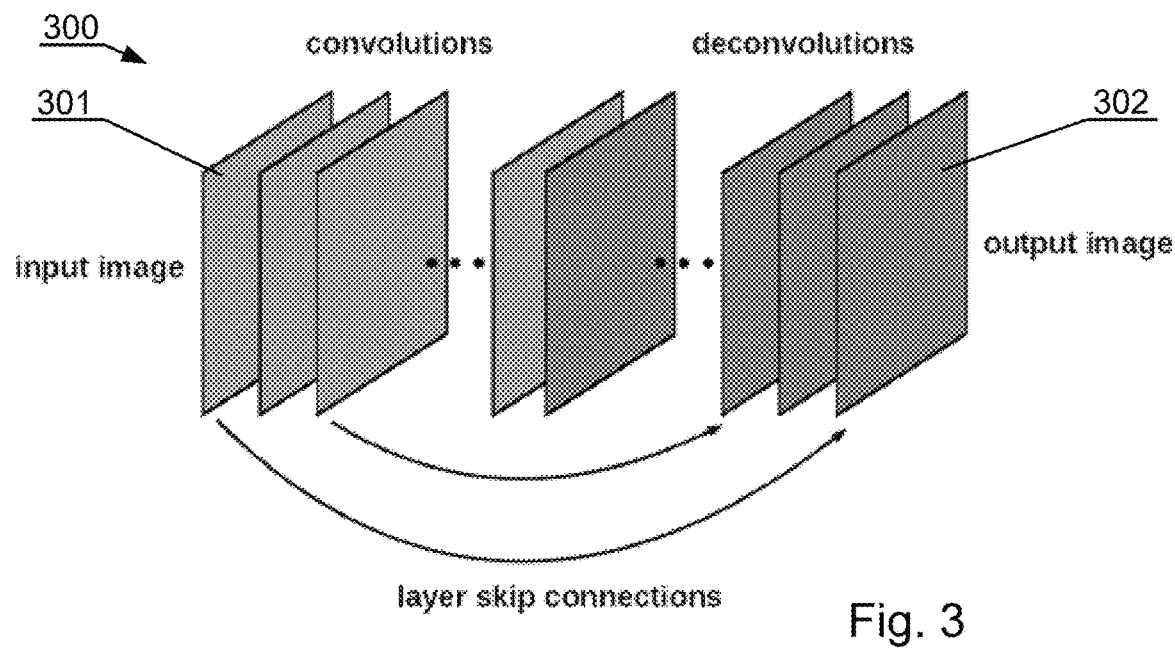
FIG. 3 shows a denoising CNN architecture in accordance with an embodiment of the invention.

The following detailed description is of the best currently contemplated modes of carrying out the invention. The description is not to be taken in a limiting sense, but is made merely for the purpose of illustrating the general principles of the invention.

The invention relates to processing images of a bony structure, such as a spine, skull, pelvis, long bones, shoulder joint, hip joint, knee joint etc. The foregoing description will present examples related mostly to a spine, but a skilled person will realize how to adapt the embodiments to be applicable to the other bony structures as well.

Moreover, the invention may include, before segmentation, pre-processing of lower quality images to improve their quality. For example, the lower quality images may be low dose computer tomography (LDCT) images or magnetic resonance images captured with a relatively low power scanner. The foregoing description will present examples related to computer tomography (CT) images, but a skilled person will realize how to adapt the embodiments to be applicable to other image types, such as magnetic resonance images.

FIGS. 1A-1E show examples of various CT images of a spine. FIGS. 1F-1J show their corresponding segmented images obtained by the method presented herein.

FIGS. 2A and 2B show an enlarged view of a CT scan, wherein FIG. 2A is an image with a high noise level (such as a low dose (LDCT) image) and FIG. 2B is an image with a low noise level (such as a high dose (HDCT) image or an LDCT image denoised according to the method presented herein).

FIG. 2C shows a low strength magnetic resonance scan of a neck portion and FIG. 2D shows a higher strength magnetic resonance scan of the same neck portion (wherein FIG. 2D is also the type of image that is expected to be obtained by performing denoising of the image of FIG. 2C).

Therefore, in the invention, a low-dose medical images (such as shown in FIGS. 2A, 2C) is pre-processed to improve its quality to the quality level of a high-dose or high quality medical images (such as shown in FIGS. 2B, 2D), without the need to expose the patient to the high dose images.

For the purposes of this disclosure, the LDCT image is understood as an image which is taken with an effective dose of X-ray radiation lower than the effective dose for the HDCT image, such that the lower dose of X-ray radiation causes appearance of higher amount of noise on the LDCT image than the HDCT image. LDCT images are commonly captured during intra-operative scans to limit the exposure of the patient to X-ray radiation.

As seen by comparing FIGS. 2A and 2B, the LDCT image is quite noisy and is difficult to be automatically processed by a computer to identify the components of the anatomical structure.

The system and method disclosed below use a neural network and deep-learning based approach. In order for any neural network to work, it must first learn the task. The learning process is supervised (i.e., the network is provided with a set of input samples and a set of corresponding desired output samples). The network learns the relations that enable it to extract the output sample from the input sample. Given enough training examples, the expected results can be obtained.

In the presented system 100 and methods, for example method 200, a set of samples are generated first, wherein LDCT images and HDCT images of the same object (such as an artificial phantom or a lumbar spine) are captured using the computer tomography device. Next, the LDCT images are used as input and their corresponding HDCT images are used as desired output to teach the neutral network to denoise the images. Since the CT scanner noise is not totally random (there are some components that are characteristic for certain devices or types of scanners), the network learns which noise component is added to the LDCT images, recognizes it as noise and it is able to eliminate it in the following operation, when a new LDCT image is provided as an input to the network.

By denoising the LDCT images, the presented system and method may be used for intra-operative tasks, to provide high segmentation quality for images obtained from intra-operative scanners on low radiation dose setting.

FIG. 3 shows a convolutional neural network (CNN) architecture 300, hereinafter called the denoising CNN, which is utilized in the present method for denoising. The network comprises convolution layers 301 (with ReLU activation attached) and deconvolution layers 302 (with ReLU activation attached). The architecture is fully convolutional and it has layer skip connections. The use of a neural network in place of standard de-noising techniques provides improved noise removal capabilities. Moreover, since machine learning is involved, the network can be tuned to specific noise characteristics of the imaging device to further improve the performance. This is done during training. The architecture is general, in the sense that adopting it to images of different size is possible by adjusting the size (resolution) of the layers. The number of layers and the number of filters within layers is also subject to change, depending on the requirements of the application. Deeper networks with more filters typically give results of better quality. However, there's a point at which increasing the number of layers/filters does not result in significant improvement, but significantly increases the computation time, making such a large network impractical.

Figure 4:
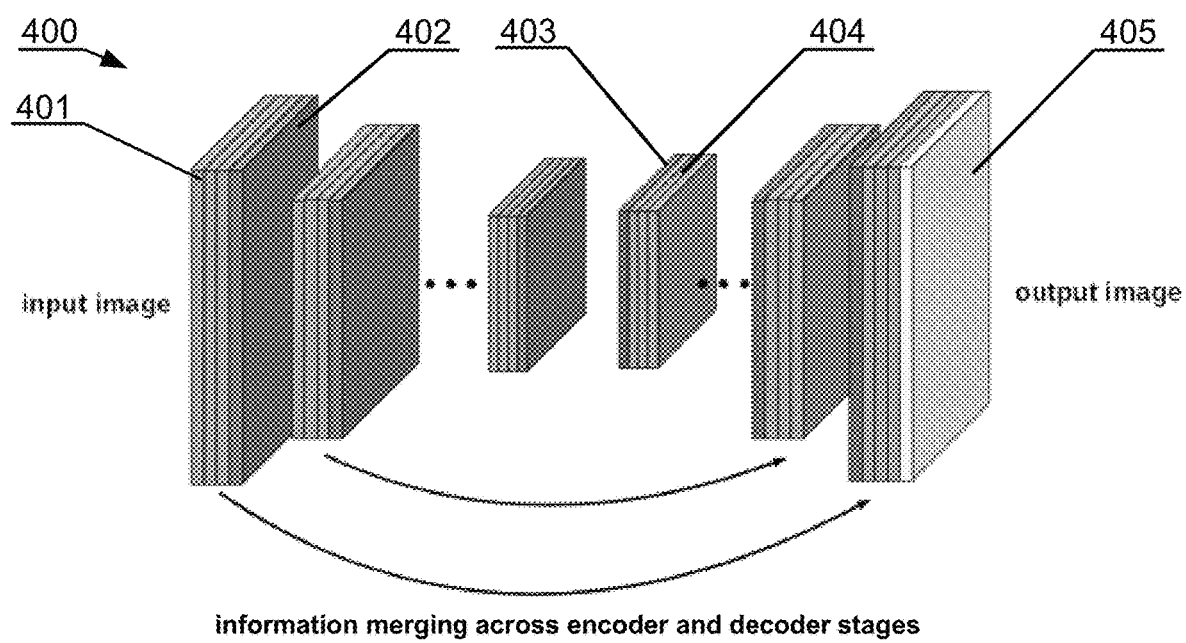
FIG. 4 shows a segmentation CNN architecture in accordance with an embodiment of the invention.

FIG. 4 shows a convolutional neural network (CNN) architecture 400, hereinafter called the segmentation CNN, which is utilized in the present method for segmentation (both semantic and binary). The architecture is fully convolutional and it has layer skip connections. The network performs pixel-wise class assignment using an encoder-decoder architecture, using as input the raw images or the images denoised with the denoising CNN. The left side of the network is a contracting path, which includes convolution layers 401 and pooling layers 402, and the right side is an expanding path, which includes upsampling or transpose convolution layers 403 and convolutional layers 404 and the output layer 405.

One or more images can be presented to the input layer of the network to learn reasoning from single slice image, or from a series of images fused to form a local volume representation.

The convolution layers 401 can be of a standard kind, the dilated kind, or a combination thereof, with ReLU or leaky ReLU activation attached.

The upsampling or deconvolution layers 403 can be of a standard kind, the dilated kind, or a combination thereof, with ReLU or leaky ReLU activation attached.

The output slice 405 denotes the densely connected layer with one or more hidden layer and a softmax or sigmoid stage connected as the output.

The encoding-decoding flow is supplemented with additional skipping connections of layers with corresponding sizes (resolutions), which improves performance through information merging. It enables either the use of max-pooling indices from the corresponding encoder stage to downsample, or learning the deconvolution filters to upsample.

The architecture is general, in the sense that adopting it to images of different size is possible by adjusting the size (resolution) of the layers. The number of layers and number of filters within a layer is also subject to change, depending on the requirements of the application.

Deeper networks typically give results of better quality. However, there is a point at which increasing the number of layers/filters does not result in significant improvement, but significantly increases the computation time and decreases the network's capability to generalize, making such a large network impractical.

The final layer for binary segmentation recognizes two classes (bone and no-bone). The semantic segmentation is capable of recognizing multiple classes, each representing a part of the anatomy. For example, for the vertebra, this includes vertebral body, pedicles, processes etc.

Figure 5:
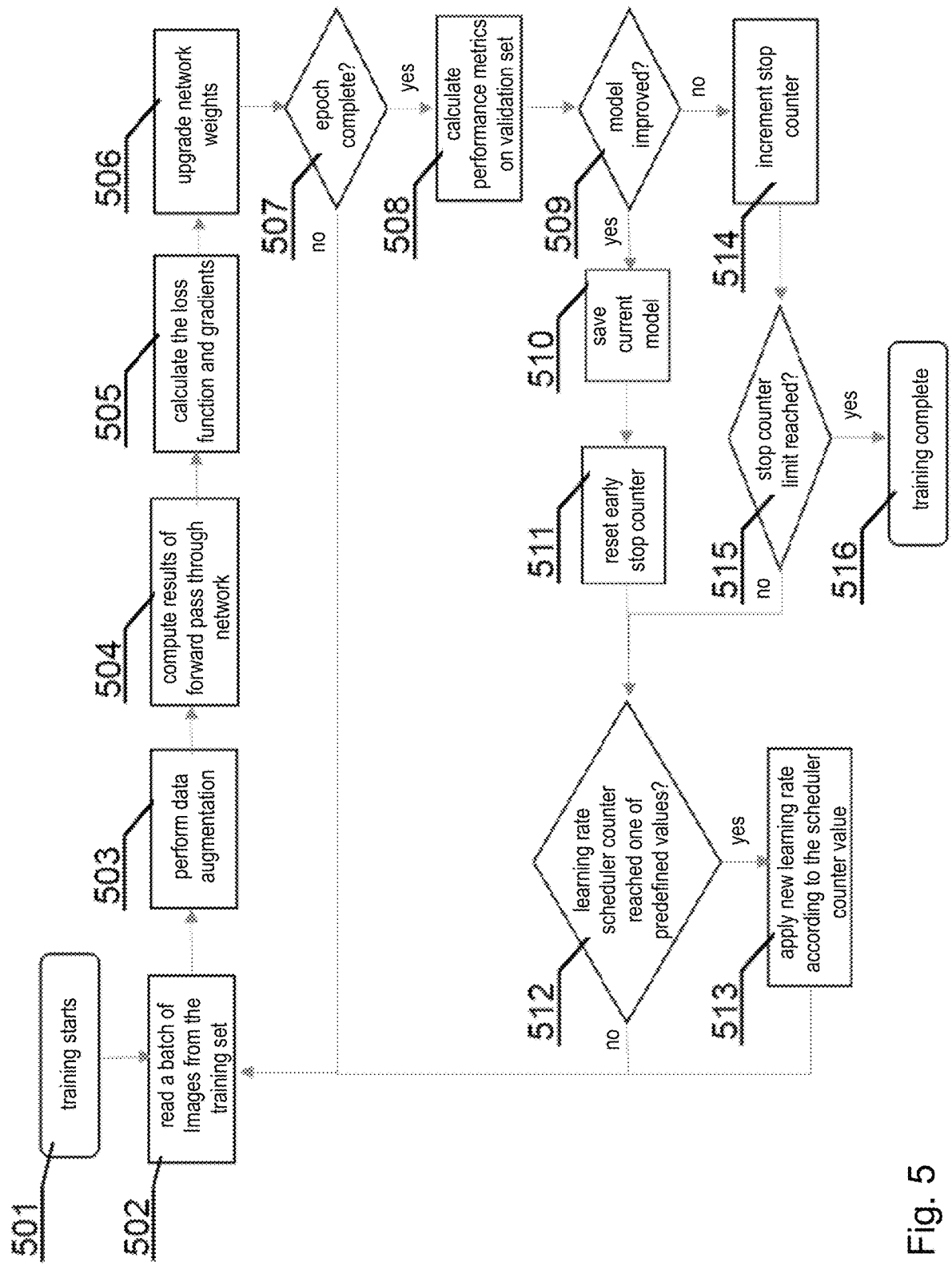
FIG. 5 shows a flowchart of a training process in accordance with an embodiment of the invention.

FIG. 5 shows a flowchart of a training process, which can be used to train both the denoising CNN 300 and the segmentation CNN 400.

The objective of the training for the denoising CNN 300 is to tune the parameters of the denoising CNN 300 such that the network is able to reduce noise in a high noise image, such as shown in FIG. 2A, to obtain a reduced noise image, such as shown in FIG. 2B.

Figures 8A, 8B:
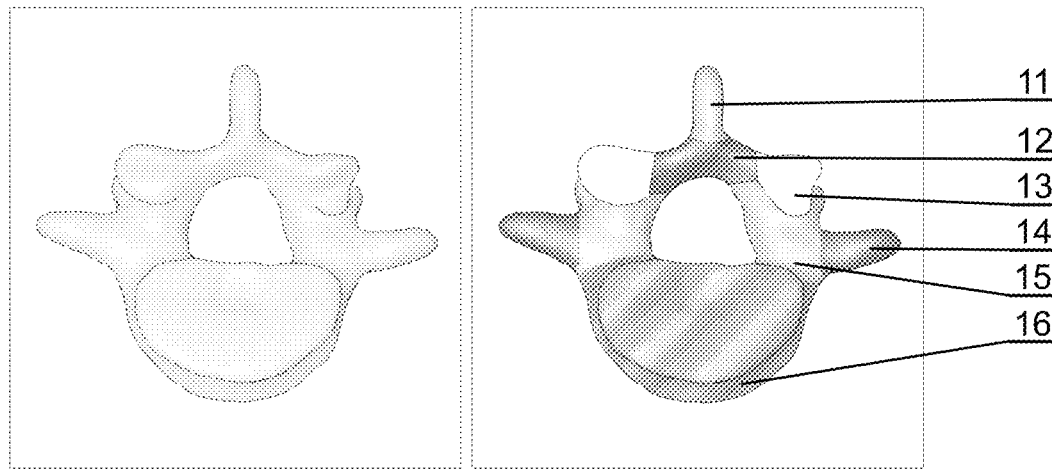
FIG. 8A shows a sample image of a CT spine scan and FIG. 8B shows a sample image of its segmentation in accordance with an embodiment of the invention.
Figure 9:
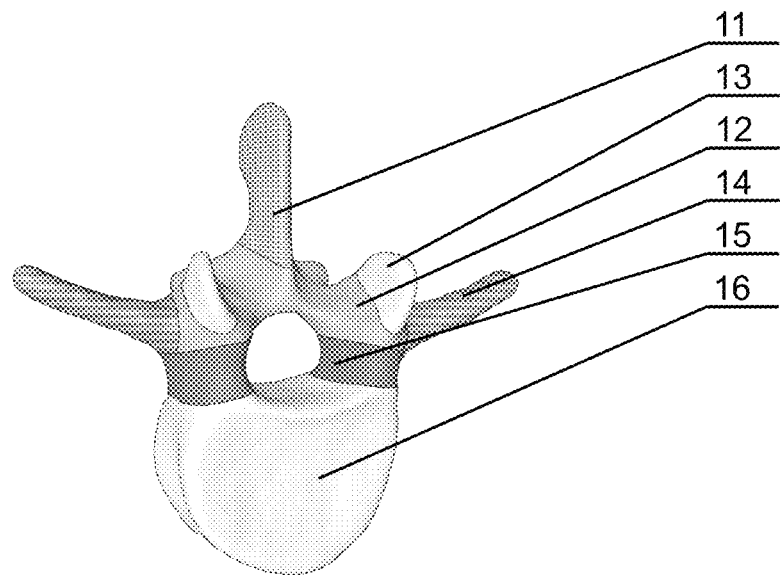
FIG. 9 shows a sample of the segmented images combined into a 3D model in accordance with an embodiment of the invention.

The objective of the training for the segmentation CNN 400 is to tune the parameters of the segmentation CNN 400 such that the network is able to recognize segments in a denoised image (such as shown in FIGS. 1A-1E or FIG. 8A) to obtain a segmented image (such as shown in FIGS. 1F-1J or FIG. 8B), wherein a plurality of such segmented images can be then combined to a 3D segmented image such as shown in FIG. 9.

The training database may be split into a training set used to train the model, a validation set used to quantify the quality of the model, and a test set.

The training starts at 501. At 502, batches of training images are read from the training set, one batch at a time. For the denoising CNN, LDCT images represent input, and HDCT images represent desired output. For the segmentation CNN, denoised images represent input, and pre-segmented (by a human) images represent output.

At 503 the images can be augmented. Data augmentation is performed on these images to make the training set more diverse. The input/output image pair is subjected to the same combination of transformations from the following set: rotation, scaling, movement, horizontal flip, additive noise of Gaussian and/or Poisson distribution and Gaussian blur, etc.

At 504, the images and generated augmented images are then passed through the layers of the CNN in a standard forward pass. The forward pass returns the results, which are then used to calculate at 505 the value of the loss function—the difference between the desired output and the actual, computed output. The difference can be expressed using a similarity metric, e.g.: mean squared error, mean average error, categorical cross-entropy or another metric.

At 506, weights are updated as per the specified optimizer and optimizer learning rate. The loss may be calculated using a per-pixel cross-entropy loss function and the Adam update rule.

The loss is also back-propagated through the network, and the gradients are computed. Based on the gradient values, the network's weights are updated. The process (beginning with the image batch read) is repeated continuously until an end of the training session is reached at 507.

Then, at 508, the performance metrics are calculated using a validation dataset—which is not explicitly used in training set. This is done in order to check at 509 whether not the model has improved. If it isn't the case, the early stop counter is incremented at 514 and it is checked at 515 if its value has reached a predefined number of epochs. If so, then the training process is complete at 516, since the model hasn't improved for many sessions now, so it can be concluded that the network started overfitting to the training data.

If the model has improved, the model is saved at 510 for further use and the early stop counter is reset at 511. As the final step in a session, learning rate scheduling can be applied. The session at which the rate is to be changed are predefined. Once one of the session numbers is reached at 512, the learning rate is set to one associated with this specific session number at 513.

Once the training is complete, the network can be used for inference, i.e. utilizing a trained model for prediction on new data.

Figure 6:
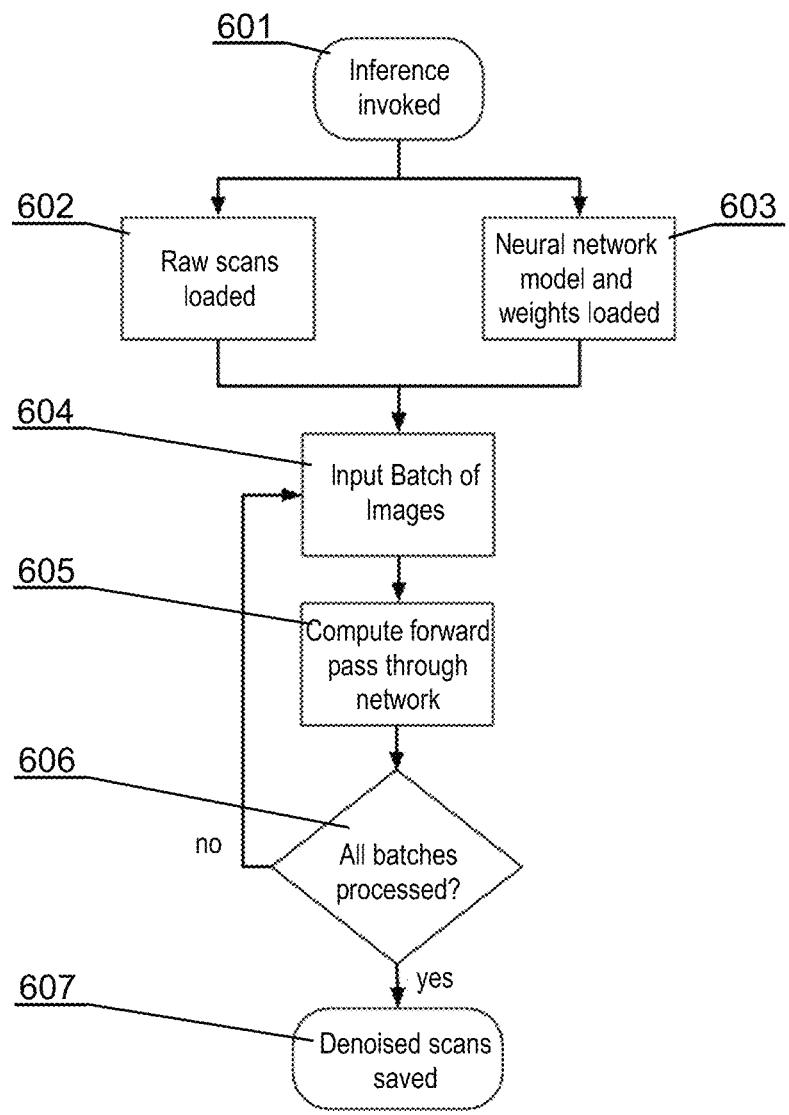
FIG. 6 shows a flowchart of an inference process for the denoising CNN in accordance with an embodiment of the invention.

FIG. 6 shows a flowchart of an inference process for the denoising CNN 300.

After inference is invoked at 601, a set of scans (LDCT, not denoised) are loaded at 602 and the denoising CNN 300 and its weights are loaded at 603.

At 604, one batch of images at a time is processed by the inference server. At 605, a forward pass through the denoising CNN 300 is computed.

At 606, if not all batches have been processed, a new batch is added to the processing pipeline until inference has been performed at all input noisy LDCT images.

Finally, at 607, the denoised scans are saved.

Figure 7:
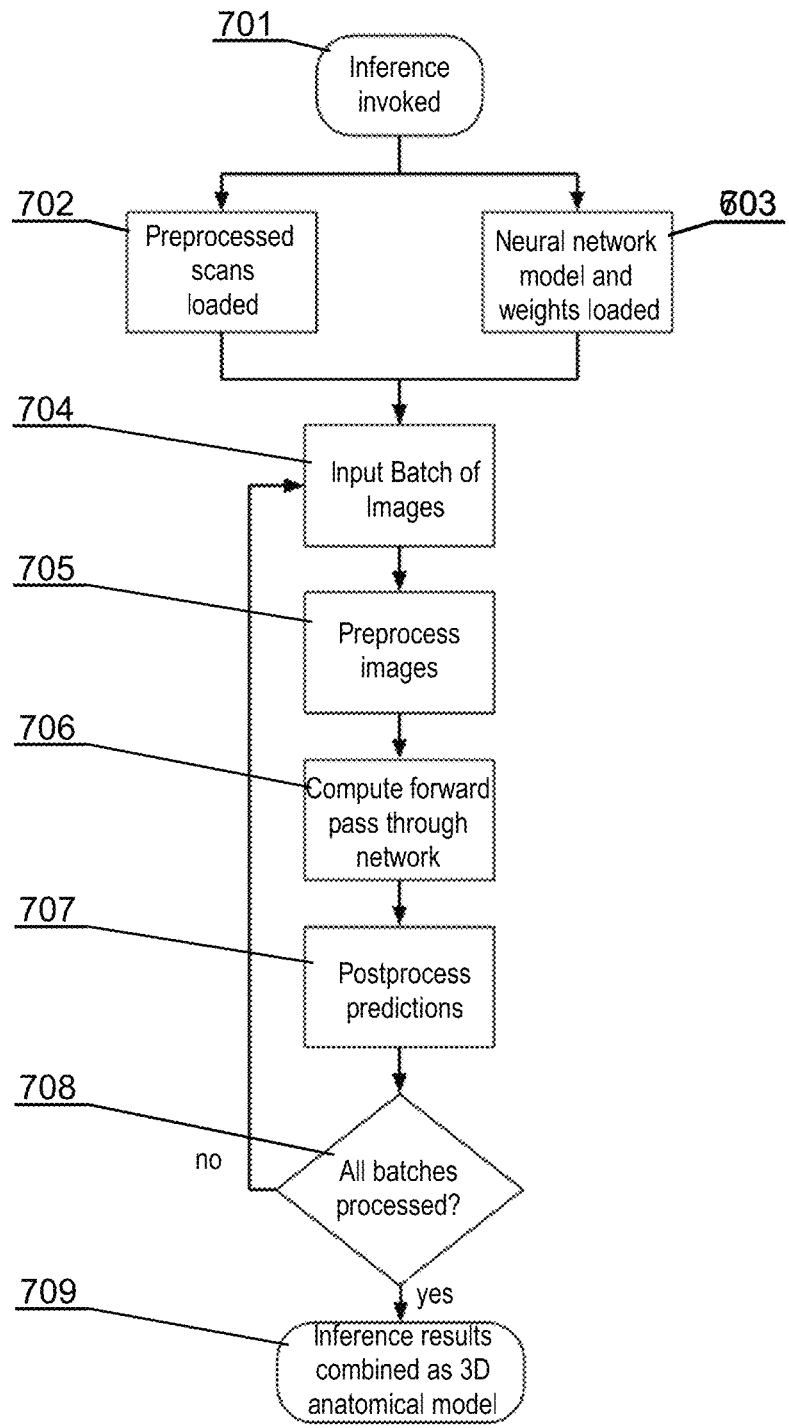
FIG. 7 shows a flowchart of an inference process for the segmentation CNN in accordance with an embodiment of the invention.

FIG. 7 shows a flowchart of an inference process for the segmentation CNN 400.

After inference is invoked at 701, a set of scans (denoised images obtained from noisy LDCT images) are loaded at 702 and the segmentation CNN 400 and its weights are loaded at 703.

At 704, one batch of images at a time is processed by the inference server.

At 705, the images are preprocessed (e.g., normalized, cropped) using the same parameters that were utilized during training, as discussed above. In at least some implementations, inference-time distortions are applied and the average inference result is taken on, for example, 10 distorted copies of each input image. This feature creates inference results that are robust to small variations in brightness, contrast, orientation, etc.

At 706, a forward pass through the segmentation CNN 400 is computed.

At 707, the system may perform postprocessing such as linear filtering (e.g. Gaussian filtering), or nonlinear filtering, such as median filtering and morphological opening or closing.

At 708, if not all batches have been processed, a new batch is added to the processing pipeline until inference has been performed at all input images.

Finally, at 709, the inference results are saved and can be combined to a segmented 3D model. The model can be further converted to a polygonal mesh representation for the purpose of visualization on the display. The volume and/or mesh representation parameters can be adjusted in terms of change of color, opacity, changing the mesh decimation depending on the needs of the operator.

FIG. 8A shows a sample image of a CT spine scan and FIG. 8B shows a sample image of its segmentation. Every class (anatomical part of the vertebra) can be denoted with its specific color. The segmented image comprises spinous process 11, lamina 12, articular process 13, transverse process 14, pedicles 15, vertebral body 16.

FIG. 9 shows a sample of the segmented images displaying all the parts of the vertebrae (11-16) obtained after the semantic segmentation combined into a 3D model.

Figure 10:
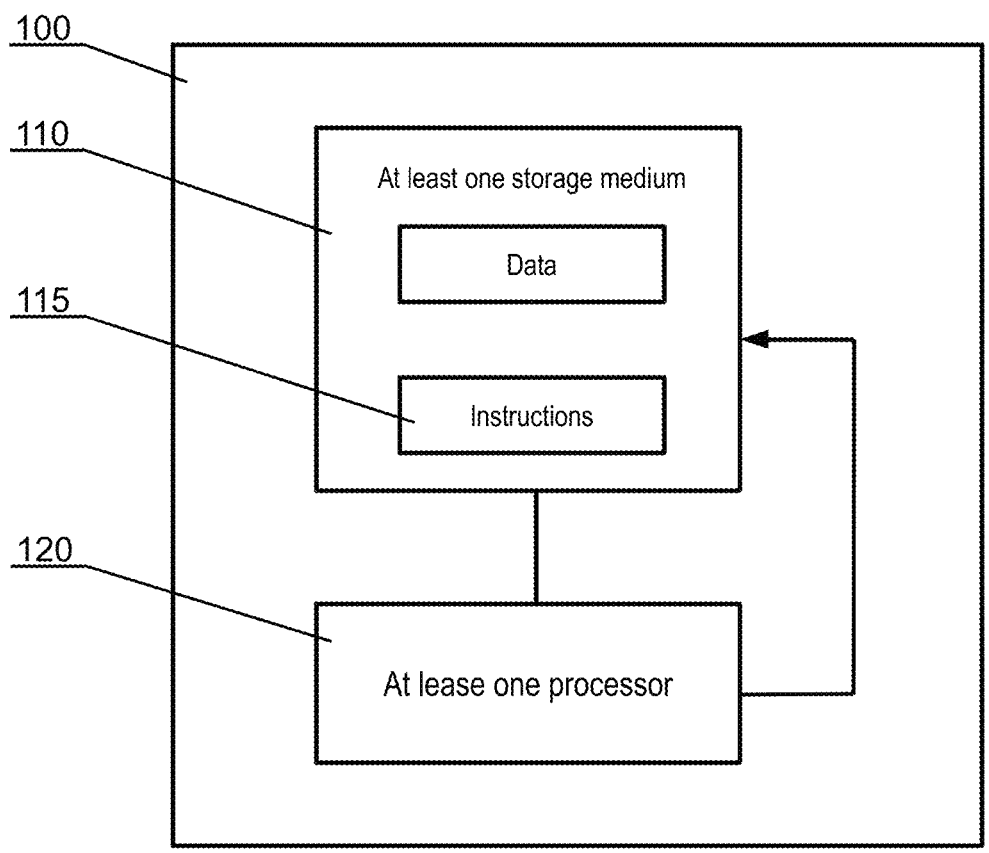
FIG. 10 shows a schematic of a system in accordance with an embodiment of the invention.

FIG. 10 shows a schematic illustration of a computer-implemented system 100, for example a machine learning system, in accordance with one embodiment of the invention. The system 100 may include at least one nontransitory processor-readable storage medium 110 that stores at least one of processor-executable instructions 115 or data; and at least one processor 120 communicably coupled to the at least one nontransitory processor-readable storage medium 110. The at least one processor 120 may be configured to (by executing the instructions 115) receive segmentation learning data comprising a plurality of batches of labeled anatomical image sets, each image set comprising image data representative of a series of slices of a three-dimensional bony structure, and each image set including at least one label which identifies the region of a particular part of the bony structure depicted in each image of the image set, wherein the label indicates one of a plurality of classes indicating parts of the bone anatomy. The at least one processor 120 may also be configured to (by executing the instructions 115) train a segmentation CNN, that is a fully convolutional neural network model with layer skip connections, to segment into a plurality of classes at least one part of the bony structure utilizing the received segmentation learning data. The at least one processor 120 may also be configured to (by executing the instructions 115) store the trained segmentation CNN in at least one nontransitory processor-readable storage medium 110 of the machine learning system.

Figure 11:
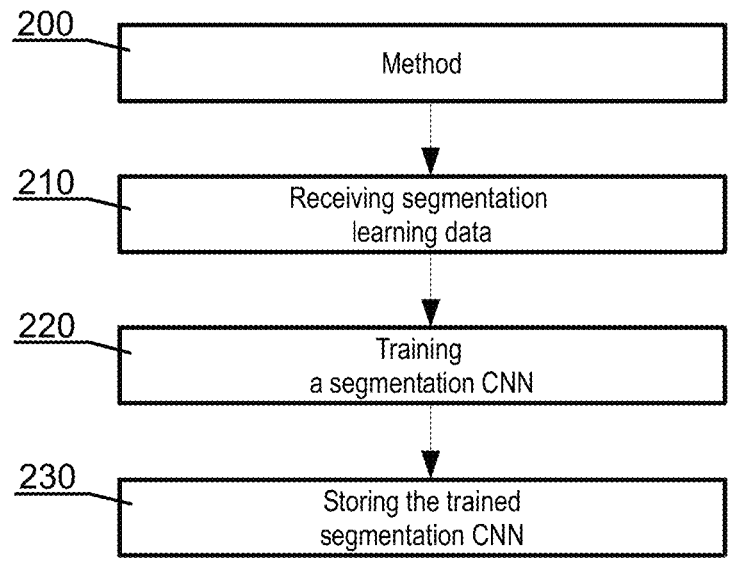
FIG. 11 is a flow chart of a method in accordance with an embodiment of the invention

FIG. 11 is a flow chart of a method 200 of automated segmentation of images of a three-dimensional bony structure. Method 200 may include a step 210 of receiving, by at least one processor communicably coupled to at least one nontransitory processor-readable storage medium that stores at least one of processor-executable instructions or data, segmentation learning data comprising a plurality of batches of labeled anatomical image sets, each image set comprising image data representative of a series of slices of the three-dimensional bony structure, and each image set including at least one label which identifies the region of a particular part of the bony structure depicted in each image of the image set, wherein the label indicates one of a plurality of classes indicating parts of the bone anatomy. Method 200 may also include a step 220 of training, by the at least one processor, a segmentation CNN, that is a fully convolutional neural network model with layer skip connections, to segment into a plurality of classes at least one part of the bony structure utilizing the received learning data. Method 200 may further include a step 230 of storing, by the at least one processor, the trained segmentation CNN in the at least one nontransitory processor-readable storage medium. The processor-executable instructions may include a module for performing each of the steps 210, 220, 230, such as a module for receiving the segmentation data in step 210, a module for training the segmentation CNN in step 220 and a module for storing the training segmentation CNN in step 230.

Figure 12:
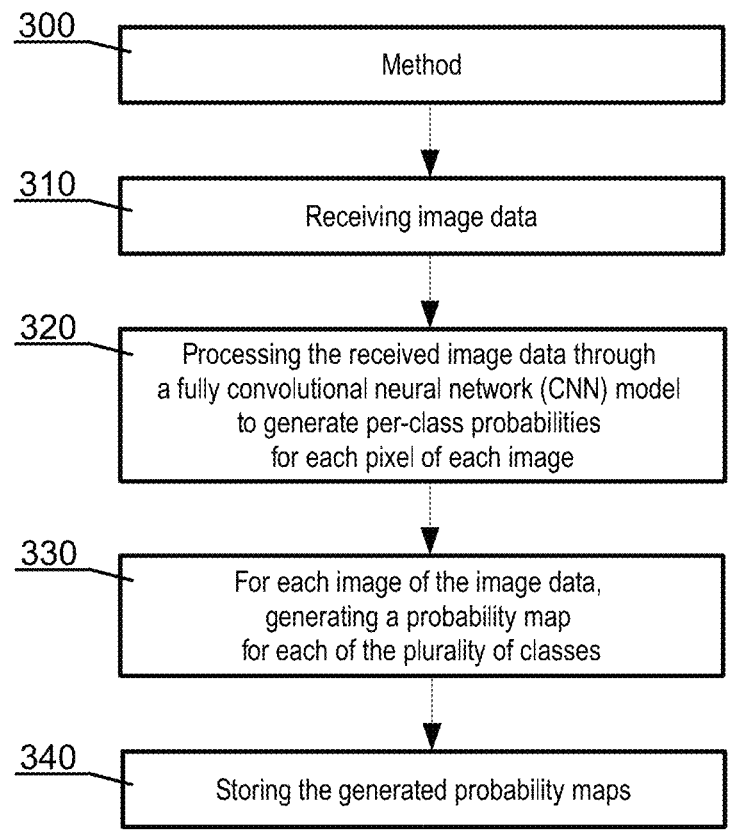
FIG. 12 is a flow chart of a further method in accordance with an embodiment of the invention.

FIG. 12 is a flow chart of a method 300 of operating a machine learning system, wherein the system includes at least one nontransitory processor-readable storage medium that stores at least one of processor-executable instructions or data, and at least one processor communicably coupled to at least one nontransitory processor-readable storage medium. Method 300 includes a step 310 of receiving, by the at least one processor, image data which represents a three-dimensional bony anatomical structure. Method 300 may also include a step 320 of processing, by the at least one processor, the received image data through a fully convolutional neural network (CNN) model to generate per-class probabilities for each pixel of each image of the image data, each class corresponding to one of a plurality of parts of the anatomical structure represented by the image data.

Method 300 may further include a step 330 of, for each image of the image data, generating, by the at least one processor, a probability map for each of the plurality of classes using the generated per-class probabilities. Method 300 may still further include a step 340 of storing, by at least one processor, the generated probability maps in the at least one nontransitory processor-readable storage medium.

Method 300 may also include processing the received image data through the CNN model wherein the CNN model includes a contracting path and an expanding path. Method 300 may also include the contracting path including a number of convolutional layers and a number of pooling layers, each pooling layer preceded by at least one convolutional layer.

The functionality described herein can be implemented in a computer system. The system may include at least one nontransitory processor-readable storage medium that stores at least one of processor-executable instructions or data and at least one processor communicably coupled to that at least one nontransitory processor-readable storage medium. That at least one processor is configured to perform the steps of the methods presented herein.

While the invention has been described with respect to a limited number of embodiments, it will be appreciated that many variations, modifications and other applications of the invention may be made. Therefore, the claimed invention as recited in the claims that follow is not limited to the embodiments described herein.

The invention claimed is:

1. A computer-implemented machine learning system, comprising:
   at least one nontransitory processor-readable storage medium that stores at least one of processor-executable instructions or data; and
   at least one processor communicably coupled to the at least one nontransitory processor-readable storage medium, wherein the at least one processor:
   receives segmentation learning data comprising a plurality of batches of labeled anatomical image sets, each image set of the plurality of batches of labeled anatomical image sets comprising image data representative of a series of slices of a three-dimensional (3D) bony structure, and each image set of the plurality of batches of labeled anatomical image sets including at least one label which identifies a region of a particular part of the 3D bony structure depicted in each image of the image set, wherein each label indicates one of a plurality of classes indicating parts of the 3D bony structure;

trains a segmentation convolutional neural network (CNN), that is a fully convolutional neural network model with layer skip connections, to segment semantically at least one part of the 3D bony structure utilizing the received segmentation learning data; and stores the trained segmentation CNN in the at least one nontransitory processor-readable storage medium of the machine learning system.

2. The system according to claim 1, wherein the at least one processor further:

receives denoising learning data comprising a plurality of batches of high quality medical images and low quality medical images, wherein the high quality medical images have a lower noise level than the low quality medical images;

trains a denoising CNN, that is a fully convolutional neural network model with layer skip connections, to denoise an image utilizing the received denoising learning data; and stores the trained denoising CNN in the at least one nontransitory processor-readable storage medium of the machine learning system.

3. The system according to claim 1, wherein the at least one processor further operates the trained segmentation CNN to process a set of input anatomical images to generate a set of output segmented anatomical images.

4. The system according to claim 2, wherein the at least one processor further operates the trained segmentation CNN to process a set of input anatomical images to generate a set of output segmented anatomical images.

5. The system according to claim 4, wherein the at least one processor further operates the trained denoising CNN to process a set of input anatomical images to generate a set of output denoised anatomical images.

6. The system according to claim 5, wherein the set of input anatomical images processed by the trained denoising CNN comprises low quality anatomical images.

7. The system according to claim 6, wherein the set of input anatomical images processed by the trained segmentation CNN comprises the set of output denoised anatomical images of the denoising CNN.

8. The system according claim 2, wherein the low quality anatomical images are low-dose computer tomography (LDCT) images or low power magnetic resonance images, and wherein the high quality anatomical images are high-dose computer tomography (HDCT) images or high power magnetic resonance images.

9. The system of claim 1, wherein the segmentation learning data comprises preoperative or intraoperative anatomical images of the 3D bony structure.

10. The system of claim 2, wherein at least one of the segmentation learning data and the denoising learning data comprise preoperative or intraoperative anatomical images of the 3D bony structure.

11. The system of claim 1, wherein the segmentation learning data comprises labeled anatomical parts of the 3D bony structure.

12. The system of claim 3, wherein the at least one processor is further configured to combine the set of output segmented anatomical images with a 3D volume of patient anatomy.

13. A method of operating a machine learning system comprising at least one nontransitory processor-readable storage medium that stores at least one of processor-executable instructions or data, and at least one processor communicably coupled to the at least one nontransitory processor-readable storage medium, the method comprising:

receiving, by the at least one processor, segmentation learning data comprising a plurality of batches of labeled anatomical image sets, each image set of the plurality of batches of labeled anatomical image sets comprising image data representative of a series of slices of a three-dimensional (3D) bony structure, and each image set of the plurality of batches of labeled anatomical image sets including at least one label which identifies the region of a particular part of the 3D bony structure depicted in each image of the image set, wherein each label indicates one of a plurality of classes indicating parts of the 3D bony structure;

training, by the at least one processor, a segmentation convolutional neural network (CNN), that is a fully convolutional neural network model with layer skip connections, to segment semantically at least one part of the 3D bony structure utilizing the received segmentation learning data; and storing, by the at least one processor, the trained segmentation CNN in the at least one nontransitory processor-readable storage medium of the machine learning system.

14. The method according to claim 13, further comprising:

receiving denoising learning data comprising a plurality of batches of high quality medical images and low quality medical images, wherein the high quality medical images have a lower noise level than the low quality medical images;

training a denoising CNN, that is a fully convolutional neural network model with layer skip connections, to denoise an image utilizing the received denoising learning data; and storing the trained denoising CNN in the at least one nontransitory processor-readable storage medium of the machine learning system.

15. The method according to claim 14, further comprising operating the trained denoising CNN to process a set of input anatomical images to generate a set of output denoised anatomical images, wherein the set of input anatomical images processed by the trained denoising CNN comprises low quality medical images.

16. The method according to claim 15, further comprising operating the trained segmentation CNN to process a set of input anatomical images to generate a set of output segmented anatomical images, wherein the set of input anatomical images processed by the trained segmentation CNN comprises the set of output denoised anatomical images of the denoising CNN.

17. The method according to claim 16, further comprising combining set of the output segmented anatomical images with a 3D volume of patient anatomy.

18. The method of claim 13, wherein the image data is first image data, the method further comprising:

receiving, by the at least one processor, second image data which represents a 3D bony structure;

processing, by the at least one processor, the second image data through the segmentation CNN to generate per-class probabilities for the plurality of classes for each pixel of each image of the second image data;

for each image of the second image data, generating, by the at least one processor, a probability map for each of the plurality of classes using the generated per-class probabilities; and storing, by the at least one processor, the generated probability map for each image of the second image data in the at least one nontransitory processor-readable storage medium.

19. The method of claim 18, wherein the segmentation CNN includes a contracting path and an expanding path.

20. The method of claim 19, wherein the contracting path includes a number of convolutional layers and a number of pooling layers in which each pooling layer is preceded by at least one convolutional layer.

* * * * *